United States Patent
Houbrechts et al.

(10) Patent No.: US 8,636,796 B2
(45) Date of Patent: Jan. 28, 2014

(54) INTRAOCULAR LENS

(75) Inventors: Yvette Appoline Joséphine Houbrechts, Grace-Hollogne (BE); Christophe Robert Marie Armand Pagnoulle, Verviers (BE); Damien Gatinel, Paris (FR)

(73) Assignee: Physiol, Angleur (BE)

( * ) Notice: Subject to any disclaimer, the term of this patent is extended or adjusted under 35 U.S.C. 154(b) by 0 days.

(21) Appl. No.: 13/322,041

(22) PCT Filed: Jan. 25, 2011

(86) PCT No.: PCT/EP2011/051003
§ 371 (c)(1), (2), (4) Date: Jun. 6, 2012

(87) PCT Pub. No.: WO2011/092169
PCT Pub. Date: Aug. 4, 2011

(65) Prior Publication Data
US 2012/0283825 A1    Nov. 8, 2012

(30) Foreign Application Priority Data
Jan. 26, 2010 (BE) .................................. 2010/0041

(51) Int. Cl.
*A61F 2/16* (2006.01)
(52) U.S. Cl.
USPC ......................................... 623/6.3; 623/6.28
(58) Field of Classification Search
USPC .............. 623/6.11, 6.23, 6.24, 6.27, 6.28, 6.3
See application file for complete search history.

(56) References Cited

FOREIGN PATENT DOCUMENTS

| | | |
|---|---|---|
| EP | 0 064 812 | 11/1982 |
| EP | 0 343 067 | 11/1989 |
| EP | 0 375 291 | 6/1990 |
| WO | WO 94/11765 | 5/1994 |
| WO | WO 01/04667 A1 | 1/2001 |
| WO | WO 2007/092949 A1 | 8/2007 |

OTHER PUBLICATIONS

International Search Report dated May 30, 2011 issued in PCT/EP2011/051003.
Written Opinion dated May 30, 2011 issued in PCT/EP2011/051003.
Davison J.A. et al., "History and Development of the Apodized Diffractive Intraocular Lens", *J. Cataract Refract Surg 32*:849-858 (May 2006).

*Primary Examiner* — William H. Matthews
(74) *Attorney, Agent, or Firm* — Scully, Scott, Murphy & Presser, PC

(57) ABSTRACT

An intraocular lens (1) including an anterior surface (4) and a posterior surface (5) and having a substantially antero-posterior optical axis (6). In this lens, one of these anterior and posterior surfaces includes a first diffractive profile (9) forming at least one first diffractive focal point (11) of order +1 on said optical axis, and a second diffractive profile (10) forming a second diffractive focal point (12) of order +1 on said optical axis which is distinct from the first diffractive focal point of order +1. At least one portion of said second diffractive profile is superposed to at least one portion of the first diffractive profile.

20 Claims, 5 Drawing Sheets

INTRAOCULAR LENS

FIELD OF THE INVENTION

The present invention relates to an intraocular lens, and in particular to an intraocular lens with a diffractive profile on an anterior or posterior face.

STATE OF THE ART

An intraocular is a lens which may be implanted in the eye, most often for replacing the crystalline lens after a cataract operation. It normally includes lateral flexible supports, so-called "haptics", used for supporting the lens in the capsular bag. An intraocular lens may be a refractive lens, a diffractive lens, or else a refractive-diffractive lens. A refractive lens converges light towards a focal point on the optical axis by refraction, while a diffractive lens creates a diffraction pattern forming one focal point on the optical axis per diffraction order. A refractive-diffractive lens combines the features of both of them.

The crystalline lens has some flexibility allowing, through the action of ciliary muscles, adaptation of the eye to far or near vision. By pulling on the edges of the crystalline lens, the ciliary muscles flatten it, thereby displacing its focal point. However, because of weakening of the ciliary muscles due to age, or because of the replacement of the crystalline lens with an intraocular lens, a patient may at least partly lose this adaptability.

In order to address this problem, several types of bi- or multi-focal intraocular lenses have been proposed.

A bi- or multi-focal refractive intraocular lens has variable refractive power, normally decreasing from the center of the lens towards an outer edge. Such intraocular lenses are sold under the brands of Iolab® NuVue®, Storz® Tru Vista®, Alcon® AcuraSee®, Ioptex®, and AMO® ReZoom®. This takes advantage of the fact that in situations where near vision is required, such as for example for reading, one normally has high luminosity, which causes closing of the iris, concealing the outer portion of the lens and only keeping the more central portion having the highest refractive power. In one alternative, the refractive intraocular lens may have an aspherical profile, so as to correct aspherical aberration of the cornea.

These purely refractive bi- or multi-focal lenses however have drawbacks. Notably, their effect is very dependent on the size of the pupil. Further, because they have several focal points, they only provide reduced contrast and may form halos, in particular, in far vision, with reduced luminosity.

An alternative is that provided by refractive-diffractive intraocular lenses. Typically, these lenses provide a refractive optical focal point of order zero for far vision, and at least one diffractive focal point of first order for near vision. Certain refractive-diffractive intraocular lenses, such as for example those developed by 3M® and those developed by AMO® and distributed under the brand of Tecnis® share the light in a substantially equal way between both of these two focal points. On the other hand, the intraocular lenses Acri.Tec® Acri.Iisa® 366D, have asymmetrical distribution of the light, with more light directed towards the focal point for far vision than for the one for near vision, with the object of improving the contrast and reducing the formation of halos in far vision.

In the article "History and development of the apodized diffractive intraocular lens", by J. A. Davison and M. J. Simpson, published in J. Cataract Refract. Surg. Vol. 32, 2006, pp. 849-858, doi: 10.1016/j.jcrs.2006.02.006, a refractive-diffractive intraocular lens is described in which the diffractive profile is apodized, having decreasing amplitude in the direction running from the optical axis towards an outer edge of the lens. This lens, sold by Alcon® under the brand ReSTOR® thereby allows a variation of the distribution of the light between the focal points for far vision and near vision according to the aperture of the pupil.

These refractive-diffractive intraocular lenses of the state of the art, however, also have certain drawbacks. Notably, they are almost purely bifocal, with a spacing between the focal point for far vision and the one for near vision such that they may be uncomfortable in intermediate vision.

Multi-focal refractive-diffractive lenses having at least one intermediate focal point have also been proposed. In International Patent Application WO 94/11765, a refractive-diffractive lens is proposed with a focal point of order zero for intermediate vision, a focal point of order +1 for near vision, and a focal point of order −1 for far vision. This lens, however, only allows a substantially equitable distribution of the light between the three focal points, independently of the pupil aperture.

In International Patent Application WO 2007/092949, an intra-ocular lens is proposed including a plurality of diffractive profiles, each with a distinct focal point of order +1. The different profiles are arranged on concentric areas, and the distribution of the light between the focal points will therefore strongly depend on the pupil size, as in refractive multi-focal intraocular lenses.

Further, all the diffractive and refractive-diffractive intraocular lenses of the state of the art have the drawback of the loss of a considerable portion of the light towards unusable focal points of an order greater than 1.

SUMMARY OF THE INVENTION

A first object of the present invention is to provide an intraocular lens having two useful diffractive focal points, with distribution of the light between both of these focal points which does not necessarily depend on the pupil size.

An intraocular lens according to the present invention includes an anterior surface and a posterior surface and has a substantially antero-posterior optical axis. In this lens, one of these anterior and posterior surfaces includes a first diffractive profile forming at least one first diffractive focal point of order +1 on said optical axis, and a second diffractive profile forming a second diffractive focal point of order +1 on said optical axis which is distinct from the first diffractive focal point of order +1, at least one portion of said second diffractive profile being superposed on at least one portion of the just diffractive profile so that the order +2 of the second diffractive profile is added to the order +1 of the first diffractive profile.

Both diffractive profiles, even superposed, continue to form distinctive diffractive focal points. It is thus possible to obtain two different focal points of order +1 without the distribution of the light between them being necessarily affected by the pupil size.

Another object of the present invention is to provide a multi-focal intraocular lens. For this, said lens may advantageously be a refractive-diffractive lens with, in said optical axis, a focal point of order zero distinct from said first and second focal point of order +1. In particular, said focal point of order zero may be a focal point for far vision, said first focal point of order +1 may be a focal point for near vision, and said second focal point or order +1 a focal point for intermediate vision.

In this way, it is possible to obtain a multi-focal intraocular lens, in particular with a focal point for far vision, a focal point for intermediate vision and a focal point for near vision, without the distribution of the light between at least two of these focal points, and in particular between the focal point for near vision and the focal point for intermediate vision, being necessarily affected by the pupil size.

Still another object of the present invention is to limit the light losses due to refraction orders greater than +1. For this, said focal point for near vision may also substantially coincide on the optical axis with a focal point of higher order than 1 formed by the second diffractive profile. In particular, said focal point of higher order may be a focal point of order +2.

Thus, the light directed towards said focal point of higher order is not lost, but is used for reinforcing a focal point of order +1, notably the focal point for near vision. In this way, the advantage of an asymmetrical distribution of the light in favour of the focal point for near vision relatively to the focal point for intermediate vision which is less important, is thereby obtained.

Advantageously, said focal point for near vision is at a distance from the focal point for far vision corresponding to between +2.5 diopters and +5 diopters, in particular between +3 diopters and +4 diopters, such as for example +3.5 diopters. This focal length allows adequate simulation of the optimum adaptability of the crystalline lens.

The proportion of the light directed towards the diffractive points of order +1 depends on the amplitude of the diffractive profile. For example, in a refractive-diffractive lens with an amplitude of the diffractive profile of one wavelength, the entirety of the light will be directed towards the diffractive focal points, but with a decrease in the amplitude, an increasing proportion of the light will be directed towards the refractive focal point. With zero amplitude of the diffractive profile, the lens will, of course, be purely refractive.

Advantageously, said second diffractive profile may have a smaller amplitude than the first diffractive profile.

Advantageously, said first and/or second diffractive profiles may be apodized with a decreasing amplitude from the optical axis towards an outer edge of the lens, in particular proportionally to the cube of the distance to the optical axis. In this way, with an increasing aperture of the lens, the distribution of the light will vary in favor of the refractive focal point, i.e. the focal point for far vision, and to the detriment of the focal points for close and intermediate vision.

Advantageously, the lens may be aspherical, so as to obtain a greater field depth.

Advantageously, said first diffractive profile and/or said second diffractive profile may be profiles of the kinoform type, with which unnecessary refractive focal points notably those of negative order may be suppressed. Even more advantageously, edges of said first and/or second diffractive profiles may be rounded, which reduces the acute angles and improves the quality of the image by reducing diffused light.

DETAILED DESCRIPTION

Details relating to the embodiments of the invention are described hereafter in an illustrative and non-restrictive way with reference to the drawings.

FIG. 1 illustrates an exemplary intraocular lens according to an embodiment of the invention.

FIG. 2 schematically illustrates the lens of FIG. 1 with a focal point for far vision, a focal point for intermediate vision and a focal point for near vision.

Figure 7A:
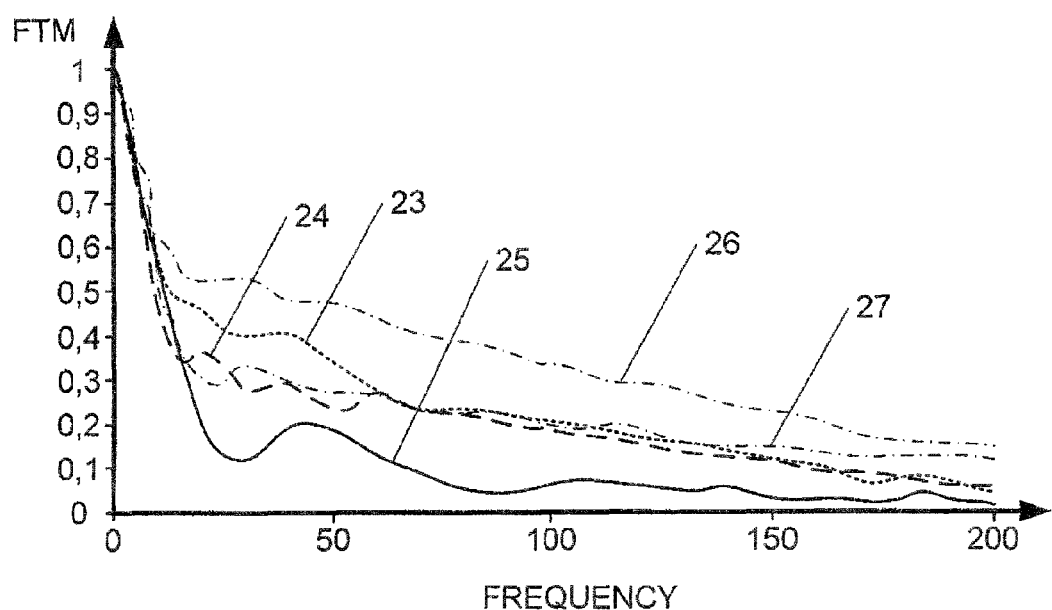

FIG. 7A compares the modulation transfer functions of the three focal points of a lens according to an embodiment of the invention, as compared with those of the two focal lengths of a bifocal lens of the state of the art, with a pupil aperture of 2.0 mm.

Figure 7B:
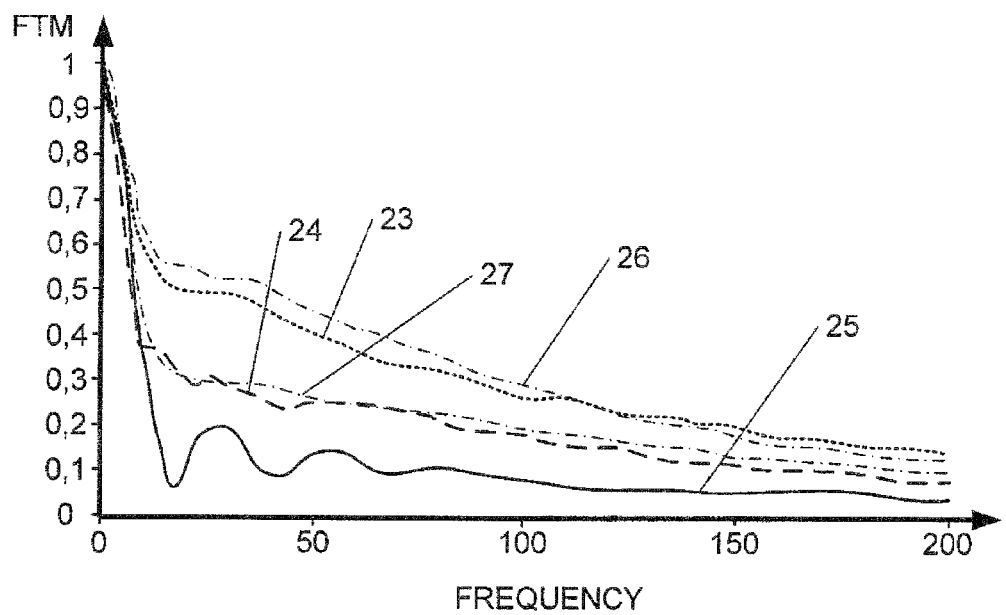
Figure 7C:
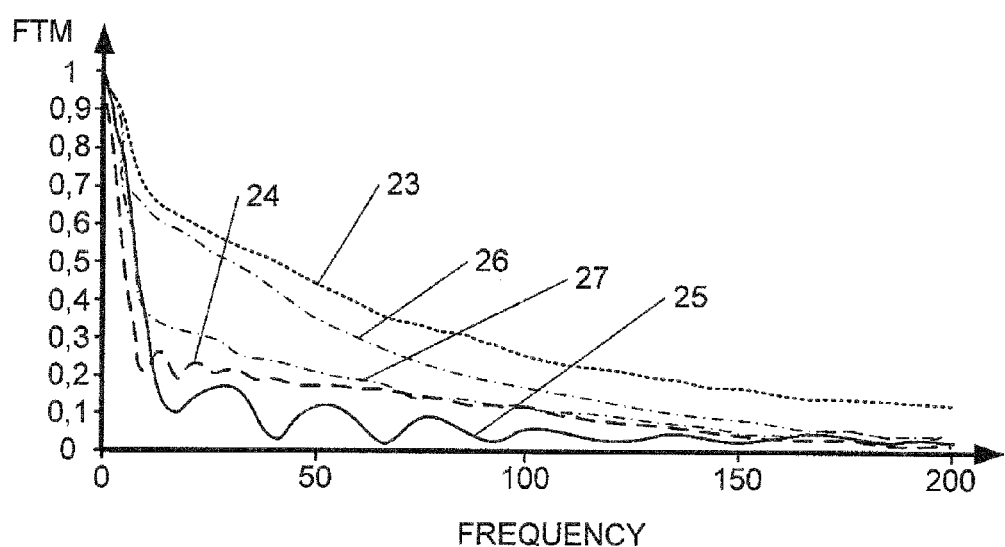

FIG. 7b compares the modulation transfer functions of the three focal points of the lens according to an embodiment of the invention, as compared with those of the two focal points of a bifocal lens of the state of the art, with a pupil aperture of 3.0 mm FIG. 7c compares the modulation transfer functions of three focal points of a lens according to an embodiment of the invention, as compared with those of the two focal points of a bifocal lens of the state of the art, with a pupil aperture of 4.5 mm.

Figure 1:
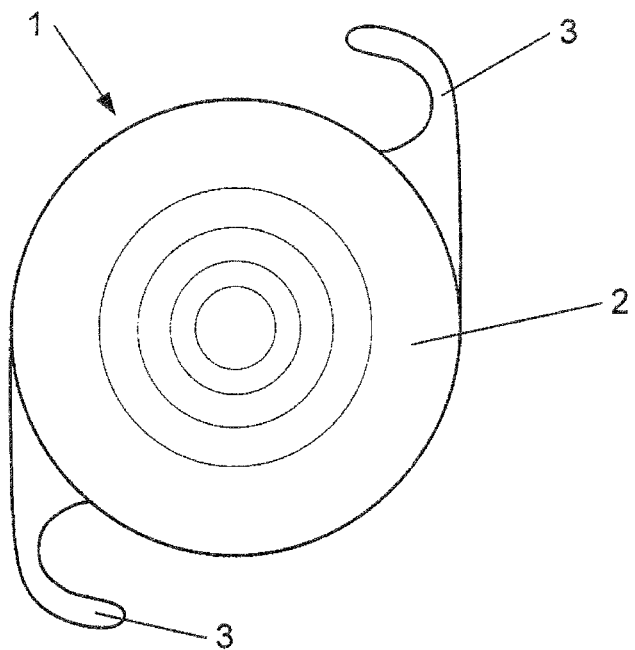

A general configuration of an intraocular lens 1 according to an embodiment of the invention is illustrated in FIG. 1. As this may be seen in the figure, the lens includes a central optical body 2 and, in this exemplary configuration, two flexible supports 3, so-called "haptics", on the outer edge of the lens 1 in order to support it in the capsular bag when it is implanted in the eye of a patient. However, other alternative configurations are known to one skilled in the art and applicable in an intraocular lens according to the invention, such as for example a larger number of haptics, loop-shaped haptics, etc.

Figure 2:
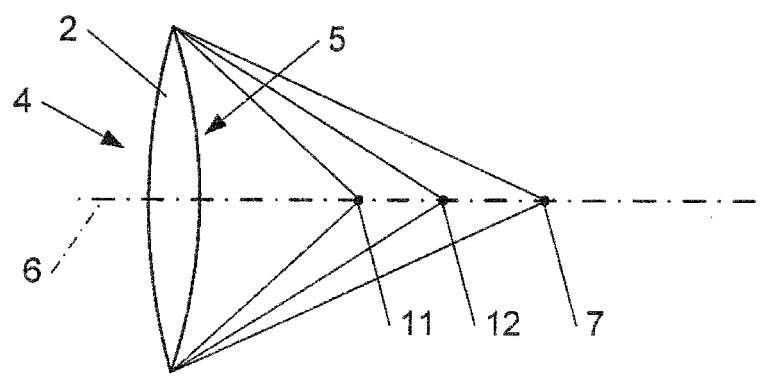

In FIG. 2, the intraocular lens 1 according to the illustrated embodiment of the invention is a lens of the refractive-diffractive type. The central optical body 2 includes an anterior face 4 and a posterior face 5, and has a substantially anteroposterior axis 6. The anterior and/or posterior faces 4,5 have curvatures such that the lens 1 directs a portion of the incident light onto a refractive focal point 7, or of order zero, on the optical axis. This focal point 7 is a focal point for far vision. In this particular embodiment, the lens 1 has an asphericity with an aspherical aberration of −0.11 μm. This asphericity ensures a natural balance between the sensitivity to the contrast and the field depth by inducing a moderate positive spherical aberration in the eye implanted with this lens.

Figure 3:
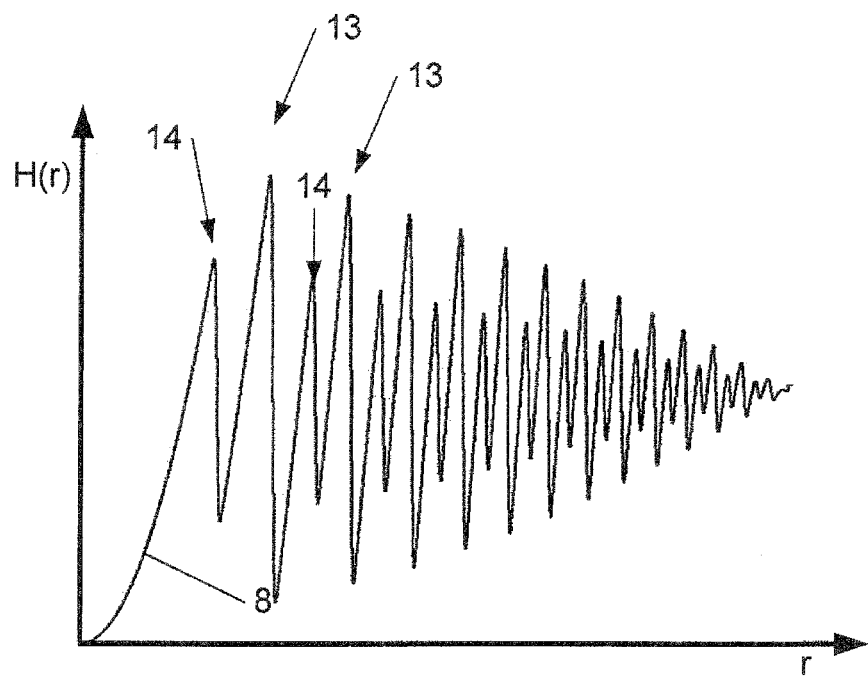
FIG. 3 illustrates the radial section of the anterior surface of the lens of FIG. 1 having two superposed diffractive profiles.
Figure 4A:
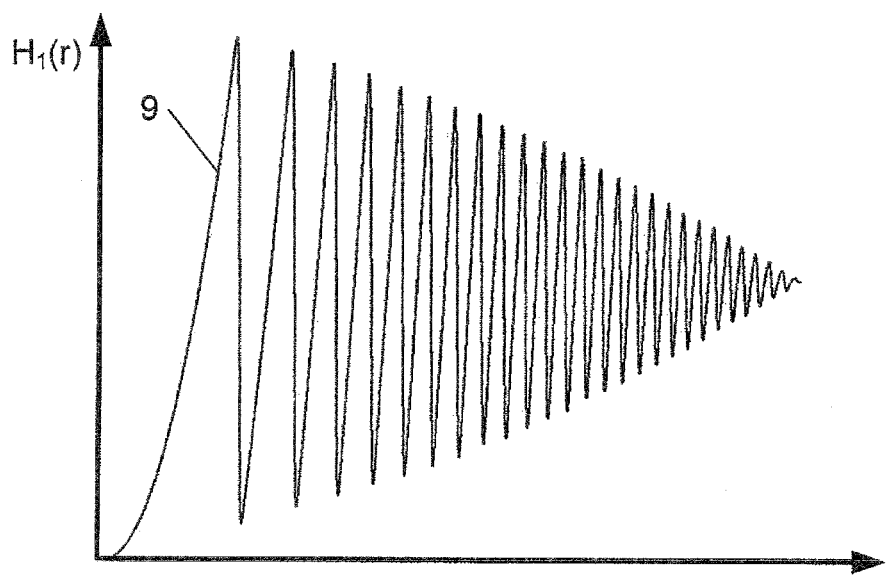
FIG. 4a illustrates a first of the two diffractive profiles of FIG. 3.
Figure 4B:
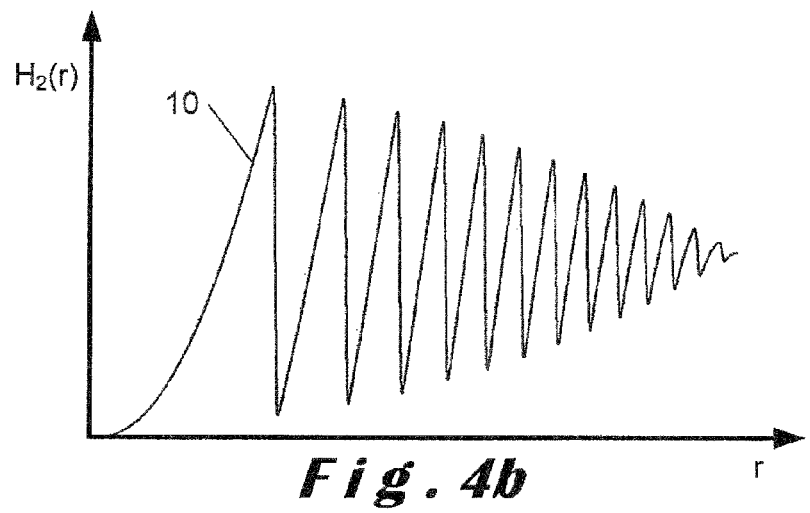
FIG. 4b illustrates a second one of the two diffractive profiles of FIG. 1.

However, on its anterior face 4, the lens 1 has a relief 8 illustrated in FIG. 3 and formed by the superposition of a first diffractive profile 9, illustrated in FIG. 4a, with a second diffractive profile 10, illustrated in FIG. 4b. (It should be noted that in these three figures, the height of the profiles is considerably exaggerated with respect to the radial distance r). The relief 8 therefore generates a complex diffraction figure, with, on the optical axis 6, a first diffractive focal point 11 of order +1 corresponding to the first diffractive profile 9, and a second diffractive focal point 11 of order +1 corresponding to the second diffractive profile 10. The first diffractive focal point 11 of order +1 is a focal point for near vision, while the second diffractive focal point 12 of order +1 is a focal point for intermediate vision.

The first diffractive profile 9 is a profile of the kinoform type, approximately fitting the function:

$$H_1(r) = a_1\left(1 - \frac{r^3}{R^3}\right)\frac{\lambda}{2\pi}\left(\frac{1}{n_2 - n_1}\right)\left(\text{mod}\left[\left(F_1 - \sqrt{r^2 + F_1^2}\right)2\frac{\pi}{\lambda}, 2\pi\right] + \pi\right)$$

In this equation, $H_1(r)$ is the height of the first diffractive profile 9 as a function of the radial distance r relatively to the optical axis, R is the radial distance from the outer edge of the lens to the optical axis, $\lambda$ is the wavelength at which the eye has greatest sensitivity (normally 550 nm), $n_1$ and $n_2$ are refractive indexes of the material of the lens and of its implantation medium, $a_1$ is an amplitude parameter (0.44 in the illustrated embodiment), and $F_1$ is the focal length of the focal point 11 of order +1 of this first diffractive profile 9 (300 mm for +3.5 diopters in this embodiment).

The second diffractive profile 10 is also a profile of the kinoform type, approximately fitting the function:

$$H_2(r) = a_2\left(1 - \frac{r^3}{R^3}\right)\frac{\lambda}{2\pi}\left(\frac{1}{n_2 - n_1}\right)\left(\text{mod}\left[\left(F_2 - \sqrt{r^2 + F_2^2}\right)2\frac{\pi}{\lambda}, 2\pi\right] + \pi\right)$$

In this equation $H_2(r)$ is the height of this second diffractive profile 10 as a function of the radial distance r with respect to the optical axis, $a_2$ is an amplitude parameter (0.27 in the illustrated embodiment) and $F_2$ is the focal length of the focal point 12 of order +1 of this second diffractive profile 10 (600 mm for +1.75 diopters in this embodiment).

It should actually be noted that, through manufacturing constraints, the actual diffractive profiles 9, 10 may only approximately fit these equations. In particular, the edges of these actual profiles will be rounded, which may be simulated by a convolution as illustrated in FIGS. 4a and 4b, and which has the additional advantage of reducing the amount of diffused light to the benefit of the optical quality of the image.

The relief 8 resulting from the superposition of both of these profiles 9, 10 therefore approximately fits the formula $H(r)=H_1(r)+H_2(r)$, as illustrated in FIG. 3. As, in this embodiment $F_2=2F_1$, the second diffractive profile 10 has periodicity half of the one of the first diffractive profile 9. The relief 8 therefore has large sawteeth 13, resulting from the addition of a step of the first profile 9 with a step of the second profile 10, alternating with small sawteeth 14, corresponding to one step out of two of the first profile 10. Further, in this way the second profile 10 forms a diffractive profile of order +2 coinciding with the focal point 11 of order +1 of the first profile 9. Thus, a portion of the light which would otherwise be lost is used here for assisting near vision.

Figure 5:
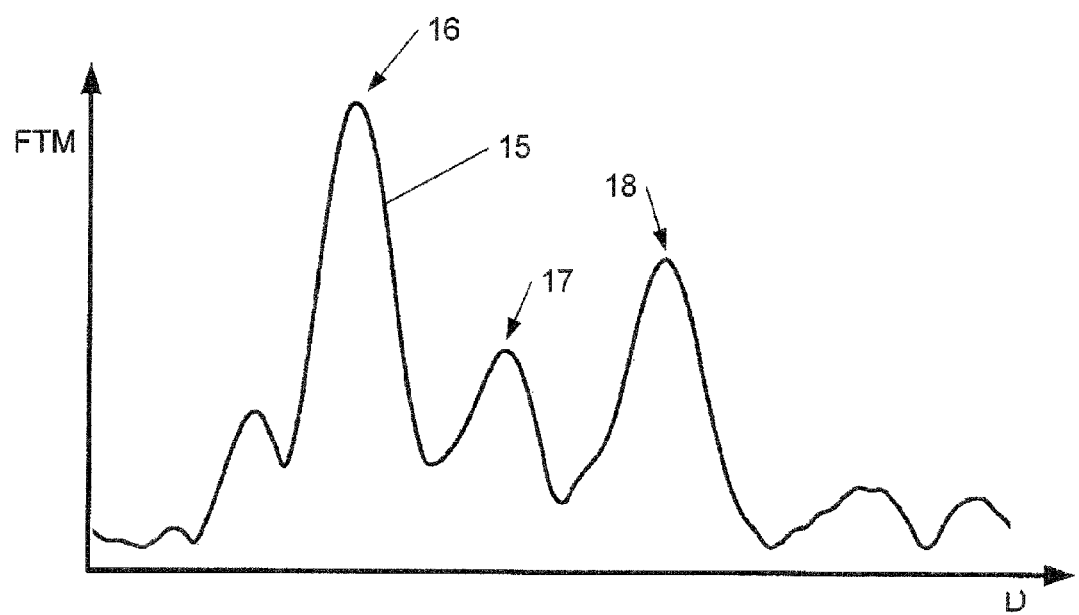
FIG. 5 illustrates the distribution of light in the optical axis of the lens of FIG. 1 for a determined pupil aperture.

A way of estimating the optical priority of an intraocular lens consists of determining experimentally its modulation transfer function (MTF). The MTF of an optical system reflects the proportion of the contrast which is transmitted through the optical system for a determined spatial frequency. Generally, the contrast decreases with an increase in the frequency. In FIG. 5, the curve 15 of the MTF of the lens 1 versus the focal power D may be seen for a pupil aperture of 3.0 mm in an eye model according to the ISO standard at 50 cycles/mm. This curve 15 shows 3 peaks 16, 17, 18 respectively corresponding to the focal point for far vision, to the focal point 12 for intermediate vision and to the focal point 11 for near vision. In this lens 1, with this aperture, the distribution of the light between these three focal points is 49% for far vision, 34% for near vision, and 17% for intermediate vision. It may also be appreciated in this figure that very little light is directed elsewhere than on these three focal points.

Figure 6:
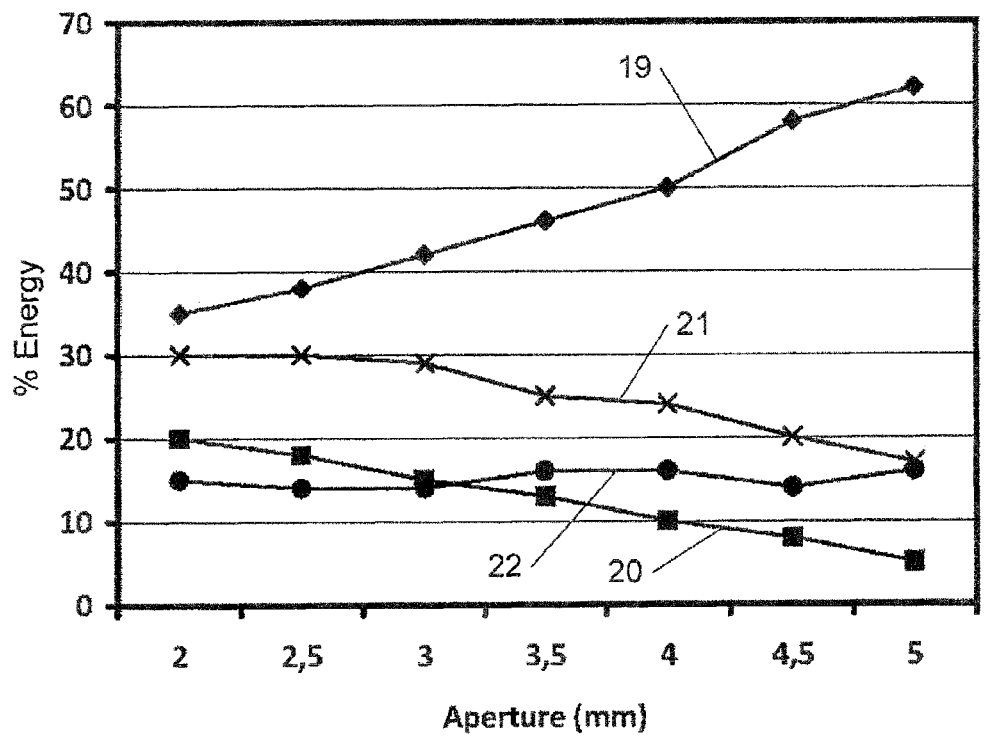
FIG. 6 illustrates the variation of the distribution of light between the three focal points depending on the pupil aperture.

As this may be seen in FIGS. 3, 4a and 4b, the amplitude of the two profiles 9, 10 decreases with the cube of the radius r, according to the equations for $H_1(r)$ and $H_2(r)$. The relief 8 is therefore "apodized" so as to decrease from the center of the lens 1 to its outer edge. Thus, with increasing aperture, increasingly more light will be directed towards the refractive focal point 7, to the detriment of the diffractive focal points 11 and 12. This may be appreciated in FIG. 6, in which the curve 19 corresponds to the percentage of incident light directed towards the focal point 7 for far vision, the curve 20 corresponds to the one directed towards the focal point 12 for intermediate vision, the curve 21 to the one directed towards the focal point 11 for near vision, and the curve 22 to the one of the light energy which is lost, as theoretically calculated according to a pupil aperture in millimeters.

In FIGS. 7a, 7b, and 7c, an exemplary intraocular lens 1 according to an embodiment of the invention was compared with a bifocal intraocular lens Acri.Tec® Acri.Iisa® 366D, considered as one of the best of the state of the art. Curves 23, 24 and 25 correspond to the MTFs versus spatial frequency for the focal point 7 for far vision, the focal point 11 for near vision, and the focal point 12 for intermediate vision, respectively. Curves 26 and 27 correspond to the MTFs versus spatial frequency for the focal points for far vision and near vision respectively of a bifocal intraocular lens Acri.Tec® Acri.Iisa® 366D, illustrated as a comparison.

FIG. 7a corresponds to a pupil aperture of 2.0 mm. It will be appreciated that the curve 24 corresponding to near vision, normally the most important for a small aperture such as the latter, is very similar to the curve 27 of the lens of the state of the art. However, the lens 1 according to this exemplary embodiment of the invention has the advantage of also having a focal point 12 for intermediate vision. With this aperture, the lens 1 has a theoretical distribution of light energy of 41% for far vision, 35% for near vision, and 24% for intermediate vision. As a comparison, the Acri.lisa® lens of the state of the art has a distribution of 65% for far vision and 35% for near vision.

FIG. 7b corresponds to a pupil aperture of 3.0 mm. In this case, the curve 24 corresponding to near vision with the lens 1 continues to be very similar to the curve 27 of the lens of the state of the art, while the curve 23 for far vision is close to the reference curve 26 corresponding to far vision with the Acri.Iisa® lens. At this aperture, the theoretical distribution of the light between the focal points 7, 12 and 11 is 49%/34%/17%, as compared with further 65%/35% for the Acri.lisa® reference lens.

Finally, FIG. 7c corresponds to a pupil aperture of 4.5 mm. In this case, the curve 23 of MTF for far vision of the lens 1 exceeds the corresponding curve 26 of the reference lens Acri.lisa®. On the other hand, the curve 24 for near vision remains quite close to the reference curve 27, in particular for medium and high spatial frequencies. In this case, the theoretical distribution of the light between the focal points 7, 12 and 11 is 67%/24%/9%, against further 65%/35% for the reference lens.

Although the present invention has been described with reference to specific exemplary embodiments, it is obvious that modifications and changes may be carried out on these examples without modifying the general scope of the invention as defined by the claims. For example, in alternative embodiments, an intraocular lens according to the invention may have different diffractive profiles, other than kinoforms, or else with different ratios between the periodicities and distances of the two superposed diffractive profiles. These diffractive profiles may also be only superposed on a portion of the anterior or posterior surface of the lens. The lens may also have different curvatures on its anterior and/or posterior faces, or no curvature, and these curvatures may, depending on the needs, either be aspherical or not. Therefore, the description and the drawings should be considered in an illustrative sense rather than in a restrictive sense.

The invention claimed is:

1. An intraocular lens comprising: an anterior surface and a posterior surface and having a substantially antero-posterior optical axis wherein one of these anterior and posterior surfaces includes a first diffractive profile forming at least one first diffractive focal point of order +1 on said optical axis, and a second diffractive profile forming a second diffractive focal point of order +1 on said optical axis which is distinct from said first diffractive focal point of order +1, at least one portion of said second diffractive profile being superposed on at least one portion of said first diffractive profile so that an order +2 of said second diffractive profile is added to said order +1 of said first diffractive profile.

2. An intraocular lens according to claim 1, wherein said lens is a refractive-diffractive lens with, in said optical axis, a focal point of order zero distinct from said first and second focal points of order +1.

3. An intraocular lens according to claim 2, wherein said focal point of order zero is a focal point for far vision, said first focal point of order +1 is a focal point for near vision, and said second focal point of order +1 is a focal point for intermediate vision.

4. An intraocular lens according to claim 3, wherein said focal point for near vision also substantially coincides on the optical axis with a focal point of higher order than +1 formed by the second diffractive profile.

5. An intraocular lens according to claim 3, wherein said focal point for near vision is at a distance from the focal point for far vision corresponding to inbetween +2.5 diopters and +5 diopters.

6. An intraocular lens according to claim 5, wherein said focal point for near vision is at a distance from the focal point for far vision corresponding to inbetween +3 diopters and +4 diopters.

7. An intraocular lens according to claim 3, wherein said second diffractive profile has a smaller amplitude than the first diffractive profile.

8. An intraocular lens according to claim 3, wherein said first and/or second diffractive profiles are apodized with decreasing amplitude from the optical axis to an outer edge of the lens.

9. An intraocular lens according to claim 8, wherein said amplitude decreases proportionally to the cube of the radial distance to the optical axis.

10. An intraocular lens according to claim 2, wherein said lens is aspherical.

11. An intraocular lens according to claim 1, wherein said first diffractive profile and/or said second diffractive profile are profiles of the kinoform type.

12. An intraocular lens according to claim 11, wherein edges of said first and/or second diffractive profiles are rounded.

13. An intraocular lens according to claim 4, wherein said focal point for far vision is at a distance from the focal point for near vision corresponding to inbetween +2.5 diopters and +5 diopters.

14. An intraocular lens according to claim 13, wherein said focal point for near vision is at a distance from the focal point for far vision corresponding to inbetween +3 diopters and +4 diopters.

15. An intraocular lens according to claim 4, wherein said second diffractive profile has a smaller amplitude than the first diffractive profile.

16. An intraocular lens according to claim 4, wherein said first and/or second diffractive profiles are apodized with decreasing amplitude from the optical axis to an outer edge of the lens.

17. An intraocular lens according to claim 16, wherein said amplitude decreases proportionally to the cube of the radial distance to the optical axis.

18. An intraocular lens according to claim 3, wherein said first diffractive profile and/or said second diffractive profile are profiles of the kinoform type.

19. An intraocular lens according to claim 18, wherein edges of said first and/or second diffractive profiles are rounded.

20. An intraocular lens according to claim 5, wherein said lens is aspherical.

* * * * *